United States Patent
Nagao

(10) Patent No.: US 12,235,343 B2
(45) Date of Patent: Feb. 25, 2025

(54) RADAR APPARATUS

(71) Applicant: Yoshimitsu Nagao, Tokyo (JP)

(72) Inventor: Yoshimitsu Nagao, Tokyo (JP)

( * ) Notice: Subject to any disclaimer, the term of this patent is extended or adjusted under 35 U.S.C. 154(b) by 350 days.

(21) Appl. No.: 17/830,379

(22) Filed: Jun. 2, 2022

(65) Prior Publication Data

US 2023/0393258 A1  Dec. 7, 2023

(51) Int. Cl.
| | |
|---|---|
| *G01S 13/50* | (2006.01) |
| *A61B 5/05* | (2021.01) |
| *A61B 5/0507* | (2021.01) |
| *A61B 5/08* | (2006.01) |
| *A61B 5/113* | (2006.01) |
| *G01S 7/41* | (2006.01) |
| *G01S 13/00* | (2006.01) |
| *G01S 13/48* | (2006.01) |

(52) U.S. Cl.
CPC .......... *G01S 13/50* (2013.01); *A61B 5/05* (2013.01); *A61B 5/0507* (2013.01); *A61B 5/0816* (2013.01); *A61B 5/1135* (2013.01); *G01S 7/415* (2013.01); *G01S 13/003* (2013.01); *G01S 13/48* (2013.01)

(58) Field of Classification Search
CPC ........ G01S 13/50; G01S 13/003; G01S 13/48; G01S 7/415; A61B 5/05; A61B 5/0507; A61B 5/0816; A61B 5/1135
See application file for complete search history.

(56) References Cited

U.S. PATENT DOCUMENTS

| | | | | |
|---|---|---|---|---|
| 2018/0024233 | A1* | 1/2018 | Searcy | G01S 13/003 342/125 |
| 2019/0231226 | A1 | 8/2019 | Kiaei | |
| 2021/0173069 | A1* | 6/2021 | Wu | G01S 13/343 |
| 2022/0146665 | A1* | 5/2022 | Vollbracht | G01S 13/88 |

FOREIGN PATENT DOCUMENTS

| | | |
|---|---|---|
| JP | 2005-278713 A | 10/2005 |
| JP | 2010-120493 A | 6/2010 |
| JP | 2021-085771 A | 6/2021 |

OTHER PUBLICATIONS

Japanese Office Action for corresponding Japanese patent application No. JP2019-215204 mailed Jun. 22, 2021 with English translation (4 pages).

\* cited by examiner

*Primary Examiner* — Timothy A Brainard
*Assistant Examiner* — Ismaaeel A. Siddiquee
(74) *Attorney, Agent, or Firm* — Harness, Dickey & Pierce, P.L.C.

(57) ABSTRACT

A radar apparatus includes: a first transmitter antenna that transmits a first electric wave having a predetermined frequency to a measurement part of an object; a second transmitter antenna that transmits a second electric wave having the same frequency as the frequency of the first electric wave to the measurement part from a position different from that of the first transmitter antenna; a receiver antenna that receives the first electric wave and the second electric wave which a constructive interference occurs between and are reflected by the measurement part, and output a reception signal; and a radar that outputs a Doppler signal according to a change in the measurement part on the basis of the reception signal, and the first transmitter antenna and the second transmitter antenna are adjusted to respective locations where the constructive interference occurs between the first electric wave and the second electric wave.

6 Claims, 7 Drawing Sheets

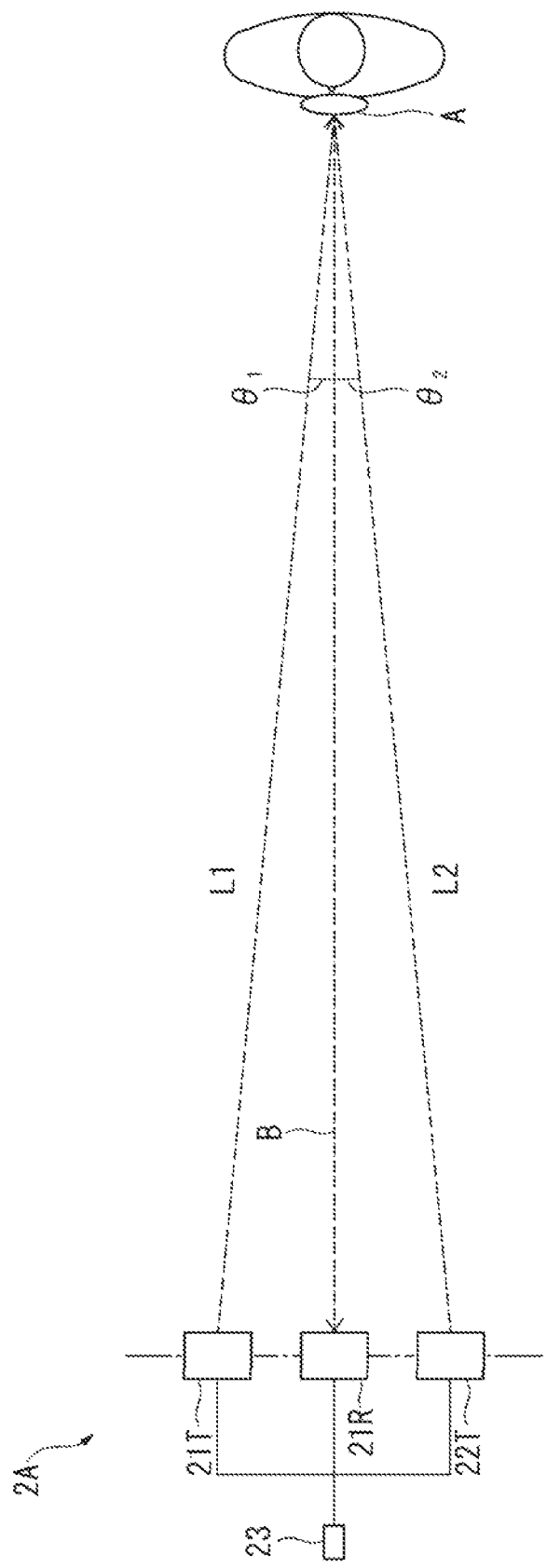

RADAR APPARATUS

BACKGROUND

Technical Field

The present invention relates to a radar apparatus that detects a change in a measurement target.

Background Art

An existing typical radar apparatus irradiates a measurement target with an electric wave and detects a change (for instance, a state of vibration or a displacement) in a measurement target by using a Doppler shift of a reflection wave reflected by the measurement target. For instance, Patent Literature 1 (JP 2010-120493 A) discloses an apparatus that irradiates a human body with a microwave, which is a type of electric wave, thereby detecting heartbeat or respiration occurring as a change in the human body.

However, a radar apparatus as described above is vulnerable to disturbance as compared with contact sensors that perform measurement while being in contact with a measurement target. For instance, application of a sudden motion to a measurement target causes a reduction in a reception amount of a reflection wave reflected by the measurement target, which results in a failure of accurate detection of a change in the measurement target in some cases.

SUMMARY OF THE INVENTION

An object of the invention is to provide a radar apparatus configured to be able to detect a change in a measurement target with a high accuracy.

A radar apparatus according to an aspect of the invention includes: a first transmitter antenna configured to transmit a first electric wave having a predetermined frequency to a measurement part of an object; a second transmitter antenna configured to transmit a second electric wave having the same frequency as the frequency of the first electric wave to the measurement part from a position different from a position of the first transmitter antenna; a receiver antenna configured to receive the first electric wave and the second electric wave which a constructive interference occurs between and are reflected by the measurement part, and output a reception signal; a radar configured to output a Doppler signal on the basis of the reception signal; and a detector configured to detect a change in the measurement part on the basis of the Doppler signal, in which the first transmitter antenna and the second transmitter antenna are adjusted to respective locations where the constructive interference occurs between the first electric wave and the second electric wave.

In the radar apparatus of the aspect of the invention, the respective electric waves (the first electric wave and the second electric wave) transmitted from the first transmitter antenna and the second transmitter antenna overlap each other near the measurement part, are reflected by the measurement part in a state where the constructive interference occurs, and are received by the receiver antenna. This causes the receiver antenna to output a reception signal affected by the above-described constructive interference and the radar to output a Doppler signal corresponding to the reception signal.

Thus, in the aspect of the invention, even when the reception amount of the reflection wave reflected by a measurement target is reduced due to disturbance or the like, the radar can stably output a Doppler signal corresponding to the state of a change in the measurement part by virtue of an increased characteristic amount according to the change in the measurement target in the reception signal. This makes it possible for the detector to detect the change in the measurement part with a high accuracy.

It is preferable that the radar apparatus of the aspect of the invention further include a first antenna unit including the first transmitter antenna; and a second antenna unit including the second transmitter antenna, the first antenna unit and the second antenna unit each including the receiver antenna.

According to the above aspect of the invention, it is possible to favorably receive an electric wave reflected by the measurement part in a state where constructive interference occurs.

BRIEF DESCRIPTION OF DRAWINGS

FIG. 7 is a schematic diagram illustrating a modification example of the above exemplary embodiment.

DESCRIPTION OF EMBODIMENT

Description will be made on an exemplary embodiment of the invention with reference to the attached drawings.

Figure 1:
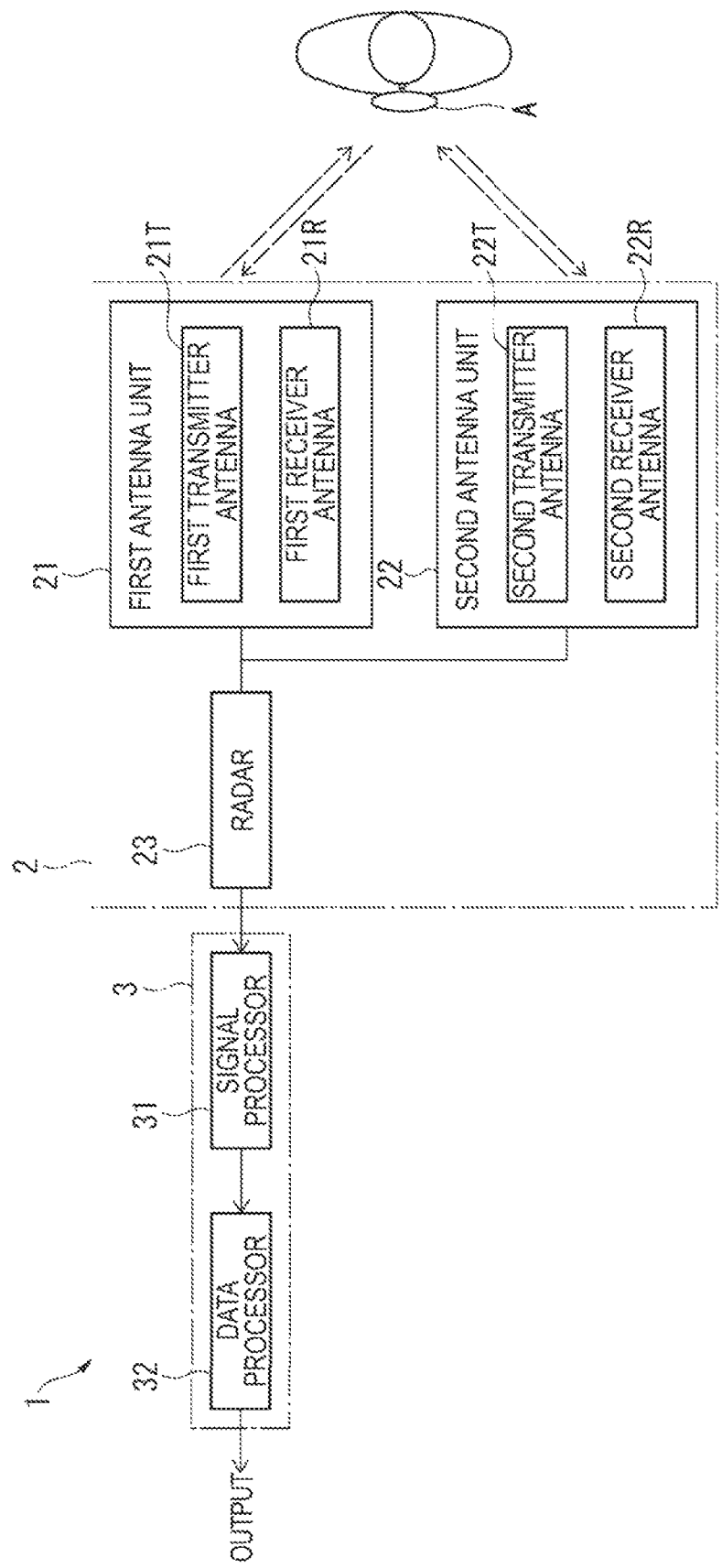
FIG. 1 is a block diagram illustrating a configuration of a radar apparatus according to an exemplary embodiment of the invention.

FIG. 1 is a block diagram illustrating a configuration of a radar apparatus 1 according to an exemplary embodiment of the invention. In the exemplary embodiment, an object to be measured by the radar apparatus 1 is a living body such as a human being or an animal and a measurement part A is a breast of the living body. Description will be made below on a case where a fine motion (a change) of a skin surface of the breast accompanying respiration of the living body.

Configuration of Radar Apparatus

As illustrated in FIG. 1, the radar apparatus 1 includes an electric wave sensor 2, which is a type of Doppler sensor, and a detector 3.

The electric wave sensor 2 includes a first antenna unit 21, a second antenna unit 22, and a radar 23.

The first antenna unit 21 includes a first transmitter antenna 21T that transmits an electric wave (a first electric wave) having a predetermined frequency to the measurement part A of the living body and a first receiver antenna 21R that receives a reflection wave reflected by the living body. The first transmitter antenna 21T and the first receiver antenna 21R each include one or more antenna elements.

Likewise, the second antenna unit 22 includes a second transmitter antenna 22T that transmits an electric wave (a second electric wave) having a predetermined frequency to the measurement part A of the living body and a second receiver antenna 22R that receives a reflection wave reflected by the living body. The second transmitter antenna 22T and the second receiver antenna 22R each include one or more antenna elements.

It should be noted that the electric wave to be transmitted from the first transmitter antenna 21T and the electric wave to be transmitted from the second transmitter antenna 22T are the same in frequency and phase.

Hereinafter, the first transmitter antenna 21T and the second transmitter antenna 22T are referred to simply as transmitter antennas 21T and 22T and the first receiver antenna 21R and the second receiver antenna 22R are referred to simply as receiver antennas 21R and 22R.

In addition, the first antenna unit 21 and the second antenna unit 22 are located at respective different positions on the living body. The locations of the first antenna unit 21 and the second antenna unit 22 will be described later in detail.

The radar 23 outputs a transmission signal of an electric wave to each of the transmitter antennas 21T and 22T and receives input of a reception signal of an electric signal from each of the receiver antenna 21R, 22R, outputting two Doppler signals (I signal and Q signal) each corresponding to a difference in frequency between the transmission signal and the reception signal.

Figure 2:
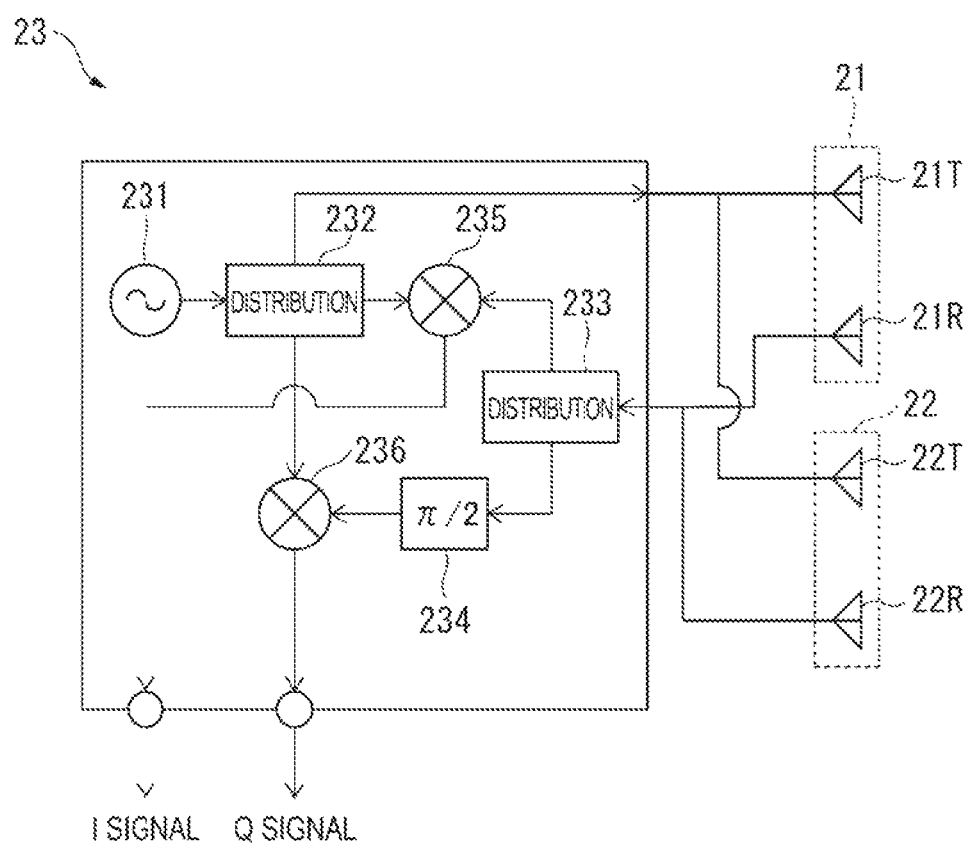
FIG. 2 is a schematic diagram illustrating a configuration of a radar of the above exemplary embodiment.

Specifically, the radar 23 includes an oscillator 231, distributors 232 and 233, a phase shifter 234, and mixers 235 and 236 as illustrated in FIG. 2. In the radar 23, the oscillator 231 oscillates the transmission signal having the predetermined frequency (for instance, 24 GHz). A transmission signal outputted from the oscillator 231 is delivered to each of the transmitter antennas 21T and 22T via the distributor 232. This causes each of the transmitter antennas 21T and 22T to transmit an electric wave (for instance, microwave).

In addition, in the radar 23, the reception signals inputted from the receiver antennas 21R and 22R are distributed through the distributor 233. Then, one of the reception signals is delivered to the mixer 235 and the other of the reception signals is shifted by $\pi/2$ (90 degrees) through the phase shifter 234 and delivered to the mixer 236. The transmission signal from the oscillator 231 is then delivered to the each of the mixers 235 and 236 via the distributor 232 and the two respective Doppler signals are obtained from the mixers 235 and 236. The two Doppler signals, that is, the reference I signal and the Q signal shifted from the I signal by 90 degrees, are to be outputted from respective output ports to the detector 3.

It should be noted that each of the I signal and the Q signal, which has a frequency proportional to a speed of the change in the measurement part A, undergoes a change in phase state depending on a state of change (approaching or receding) of the measurement part A. Specifically, the I signal is faster than the Q signal by $\pi/2$ while the measurement part A is approaching, whereas the I signal is slower than the Q signal by $\pi/2$ while the measurement part A is receding.

The detector 3 includes a signal processor 31 and a data processor 32.

The signal processor 31 applies a signal process to each of the I signal and the Q signal obtained from the radar 23, thereby obtaining respiratory signals VI and VQ each corresponding to a respiration component of the living body. A specific configuration of the signal processor 31 is not limited to a particular one. For instance, the signal processor 31 includes: a band-pass filter that extracts a frequency component (for instance, 0.1 Hz to 0.5 Hz) corresponding to respiration from the Doppler signal obtained from the radar 23; and an analog/digital converter that converts an extracted analog signal to a digital signal.

The data processor 32 includes, for instance, a calculator and a storage. The calculator reads and executes an analysis program stored in the storage to perform an analysis process of the respiratory signals VI and VQ inputted from the signal processor 31. Here, the respiratory signals VI and VQ each have a frequency proportional to the speed of the change in the measurement part A accompanying respiration of the living body and a phase difference between the respiratory signals VI and VQ corresponds to a direction of the change in the measurement part A (an approaching direction or a receding direction) accompanying respiration of the living body. The data processor 32 can thus detect the change in the measurement part A and, consequently, calculate analysis information regarding a respiration rate of the living body or the like by performing the analysis process of the respiratory signals VI and VQ.

It should be noted that a detailed description on a specific technique for the analysis process by the data processor 32 is omitted, since a known technology is usable for it.

The analysis information outputted from the data processor 32 is displayed on a display not illustrated.

In addition, in a case where the radar apparatus 1 is installed in a machine such as a vehicle and serves as an apparatus to measure a respiration rate of a driver of the vehicle, the analysis information outputted from the data processor 32 may be inputted to a control unit of the vehicle or the like. In this case, the control unit of the vehicle can determine a physical condition of the driver on the basis of the inputted analysis information and can perform a vehicle control on the basis of the physical condition of the driver, accordingly.

Behavior of Electric Wave

In a case where there are a plurality of electric wave paths from a transmission point to a reception point, a change in strength of reception of an electric wave due to a change in path length difference is usually referred to as a fading phenomenon.

For instance, in a case where a path length difference between two electric wave paths is an integral multiple of a wavelength $\lambda$, phases of respective electric waves propagating through the paths match (become the same), which causes occurrence of a constructive interference to increase the strengths of reception of the electric waves. In contrast, in a case where the path length difference between two electric wave paths is an odd multiple of one half of the wavelength $\lambda$, the phases of the electric waves propagating the paths are inverted, which causes occurrence of a destructive interference to decrease the strengths of reception of the electric waves. Therefore, a change in path length difference causes the strength of reception of an electric wave to increase or decrease, resulting in occurrence of the fading phenomenon.

Such a fading phenomenon is usually regarded as an unfavorable phenomenon and, accordingly, a technology for avoiding an influence of a fading phenomenon has been developed.

Figure 3:
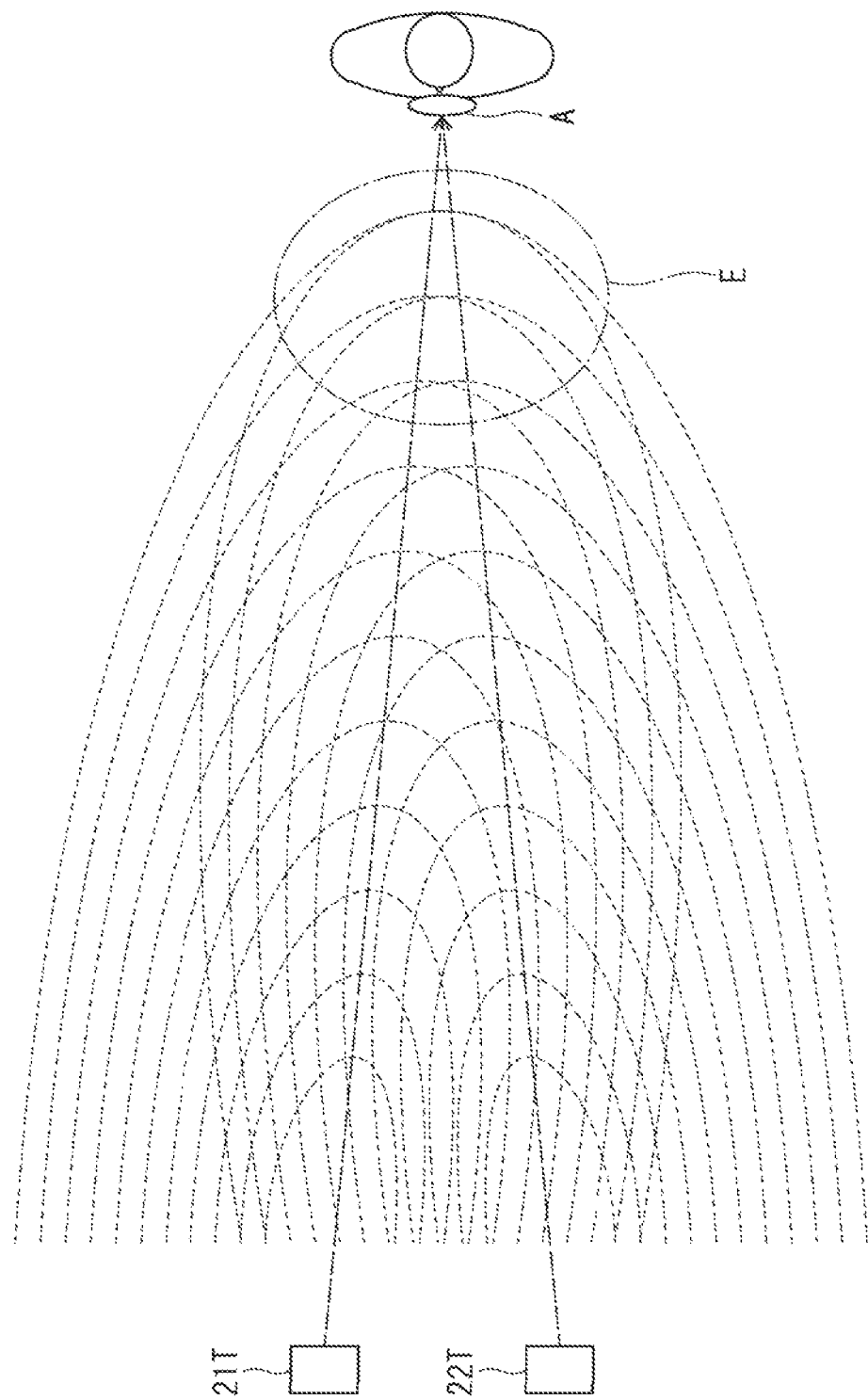
FIG. 3 is a schematic diagram for explaining interference between electric waves transmitted from two transmitter antennas of the above exemplary embodiment.

However, in the exemplary embodiment, the two transmitter antennas 21T and 22T transmit electric waves to the measurement part A from directions different from each other, thereby intentionally causing occurrence of a constructive interference of a fading phenomenon near the measurement part A. In other words, the transmitter antennas 21T and 22T are located such that the respective transmitted electric waves therefrom overlap each other near the measurement part A of the living body to cause occurrence of a constructive interference (see FIG. 3). It should be noted that an area E where the constructive interference occurs is enclosed by a broken line in the illustration in FIG. 3.

Figure 4:
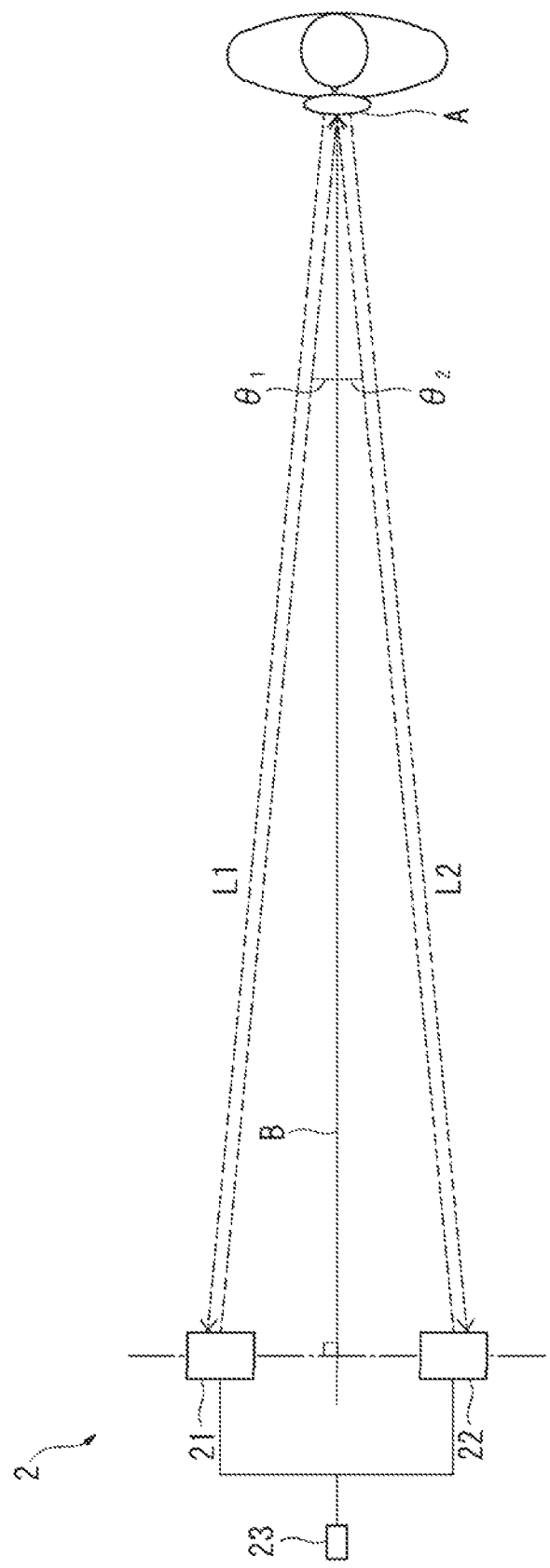
FIG. 4 is a schematic diagram for explaining locations of the two transmitter antennas of the above exemplary embodiment.

In the exemplary embodiment, the electric waves having the same phase are transmitted from the two transmitter antennas 21T and 22T. Accordingly, it is favorable that conditions for causing occurrence of a constructive interference between these electric waves include a distance L1 from the first transmitter antenna 21T to the measurement part A being equal to a distance L2 from the second transmitter antenna 22T to the measurement part A (see FIG. 4). Alternatively, since it is sufficient that, near the measurement part A, the electric wave transmitted from the first transmitter antenna 21T has the same phase as the electric wave transmitted from the second transmitter antenna 22T, a difference between the distance L1 and the distance L2 may be adjusted to be an integral multiple of the wavelength $\lambda$ of the electric wave.

To locate the transmitter antennas 21T and 22T with such conditions satisfied, at least one of the locations of the first antenna unit 21 and second antenna unit 22 may be adjusted while observing the strength of the reception signal.

In addition, in the exemplary embodiment, an angle made by a transmission direction (a first transmission direction) of the electric wave from the first transmitter antenna 21T relative to a reference line B is denoted by $\theta 1$ and an angle made by a transmission direction (a second transmission direction) of the electric wave from the second transmitter antenna 22T relative to the reference line B is denoted by $\theta 2$. It should be noted that the reference line B is a line substantially perpendicular to a surface of the measurement part A.

In this case, the angles $\theta 1$ and $\theta 2$ are adjustable as desired within ranges: 0 degrees<$\theta 1$<90 degrees and 0 degrees<$\theta 2$<90 degrees, respectively. Incidentally, the larger angles $\theta 1$ and $\theta 2$ can provide the larger area where the "constructive interference" occurs.

It should be noted that the angles $\theta 1$ and $\theta 2$ of the transmitter antennas 21T and 22T may be the same as each other or different from each other.

The respective electric waves transmitted from the transmitter antennas 21T and 22T that satisfy the above-described conditions overlap each other near the measurement part A, are reflected by the measurement part A in a state where constructive interference occurs, and are received by the receiver antennas 21R and 22R. In other words, the receiver antennas 21R and 22R output reception signals subjected to the above-described constructive interference, and the radar 23 outputs Doppler signals (the I signal and the Q signal) based on the reception signals.

Figure 5:
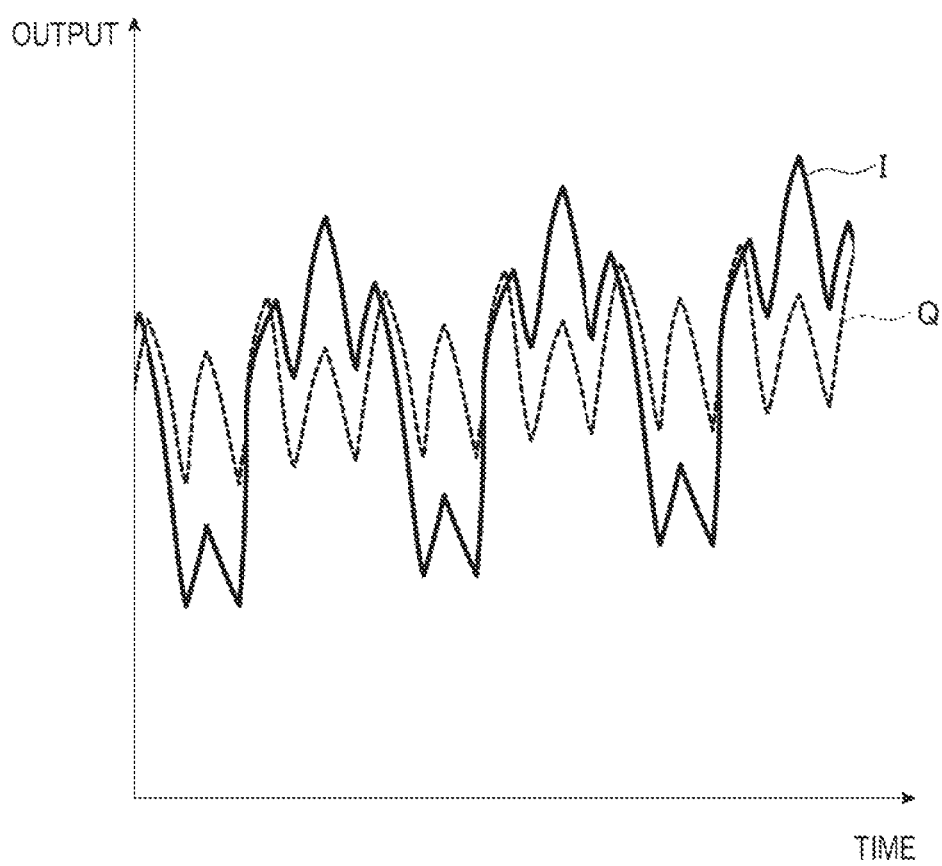
FIG. 5 is a graph illustrating a waveform example of a Doppler signal in Example of the invention.

Here, as Example of the invention, Doppler signals for measuring a change in the measurement part A were obtained by using the radar apparatus 1, where the angle $\theta 1$ in the first transmission direction and the angle $\theta 2$ in the second transmission direction were each 60 degrees (see FIG. 5).

Figure 6:
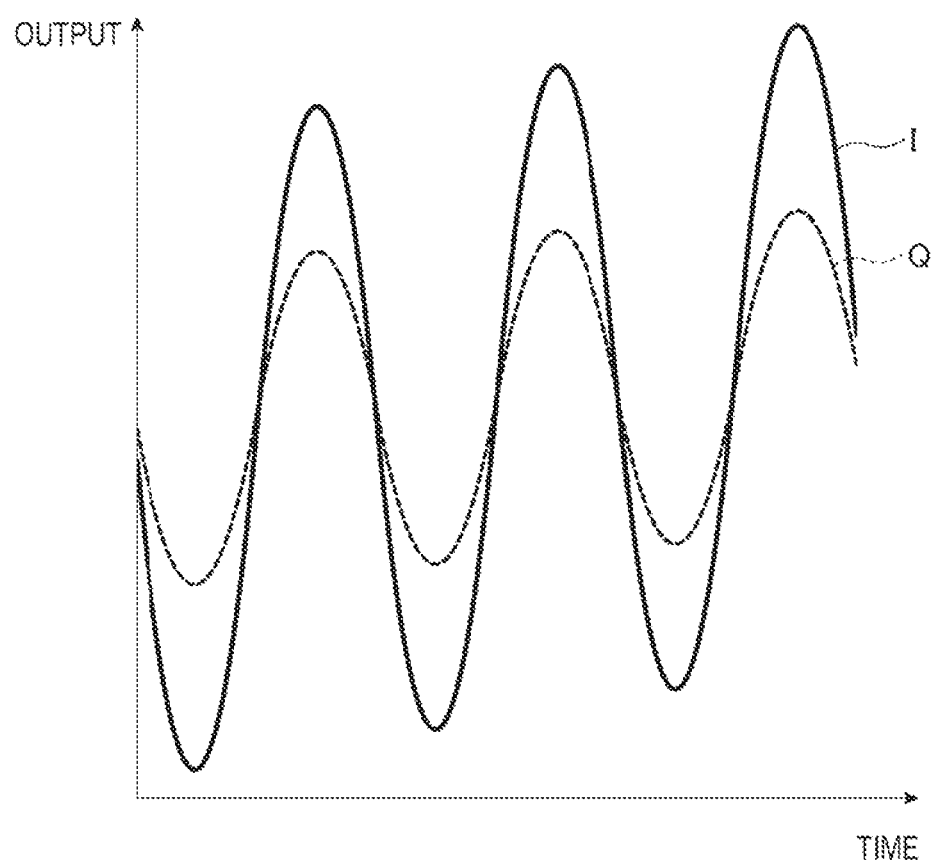
FIG. 6 is a graph illustrating a waveform example of a Doppler signal in Comparative Example of the invention.

In addition, as Comparative Example of the invention, Doppler signals for measuring a change in the measurement part A were obtained by using the radar apparatus 1, where the angle $\theta 1$ in the first transmission direction and the angle $\theta 2$ in the second transmission direction were each 0 degrees (parallel with each other) (see FIG. 6).

It should be noted that the measurement part A is a living body that is taking breath in Example and Comparative Example. In addition, FIG. 5 and FIG. 6, in which an abscissa axis is time and an ordinate axis is a signal output, show waveforms of the I signal and Q signal during measurement. The phases of the I signal and the Q signal are usually shifted from each other by 90 degrees; however, in FIG. 5 and FIG. 6, the phase shift on the graph is difficult to see due to an influence of a change in the measurement part A during measurement.

Comparing Example (FIG. 5) and Comparative Example (FIG. 6), it is found that there is a clear difference between the obtained Doppler signals.

As shown in Example (FIG. 5), since the respective reception signals of the receiver antennas 21R and 22R are subjected to the above-described constructive interference and these reception signals are brought together, an influence of disturbance (e.g., a deviation of an electric wave due to a body motion of the living body) is reduced and a characteristic amount of respiration clearly appears in each of the I signal and the Q signal outputted from the radar 23.

In contrast, in Comparative Example (FIG. 6), the above-described constructive interference does not occur between the respective reception signals of the receiver antennas 21R and 22R, and the I signal and Q signal outputted from the radar 23 each have a smaller difference from a signal obtainable when there is no respiration.

Therefore, it is clear that respiration of a living body can be measured with a higher accuracy in Example than in Comparative Example.

It should be noted that in the exemplary embodiment, the measurement part A is the breast of a living body or the like, which is a part of the living body where a fine change accompanying respiration of the living body occurs, so that, strictly speaking, a difference between the above-described adjusted distance L1 and distance L2 changes during respiration of the living body. However, the amount of the change in the measurement part A of the living body accompanying respiration is sufficiently small with respect to a width of the wavelength $\lambda$ of an electric wave used in the exemplary embodiment, so that an influence thereof on the constructive interference is ignorable.

Effects of Exemplary Embodiment

In the radar apparatus 1 of the exemplary embodiment, even when the reception amount of the reflection wave reflected by the measurement part A is reduced due to disturbance or the like, the radar 23 can stably output a Doppler signal corresponding to the state of a change in the measurement part A by virtue of the increased characteristic amount according to the change in the measurement part A in the reception signal. This makes it possible for the detector 3 to detect the change in the measurement part A with a high accuracy. In particular, the radar apparatus 1 of the exemplary embodiment is beneficial in checking whether or not a living body respires.

In addition, in the radar apparatus 1 of the exemplary embodiment, the first antenna unit 21 and the second antenna unit 22 include the transmitter antennas 21T and 22T and the receiver antennas 21R and 22R, respectively. Such a configuration makes it possible to favorably receive an electric wave reflected by the measurement part A in a state where constructive interference occurs.

Modifications

The invention is not limited to the configuration of the above-described exemplary embodiment and modifications and the like are within the scope of the invention as long as an object of the invention is achievable.

The radar apparatus 1 of the above-described exemplary embodiment includes the first antenna unit 21 and the second antenna unit 22; however, the invention is not limited thereto. For instance, the transmitter antennas 21T and 22T and the receiver antennas 21R and 22R may be separately located instead of being unitized.

In addition, the radar apparatus 1 of the above-described exemplary embodiment includes the two receiver antennas 21R and 22R but may include either one of the receiver antennas 21R and 22R. In such a modification example, the either one of the receiver antennas 21R and 22R may be located so as to be able to receive an electric wave reflected by the measurement part A (an electric wave where the first electric wave and the second electric wave overlap).

For instance, an electric wave sensor 2A of the radar apparatus of the modification example includes the two transmitter antennas 21T and 22T and the single receiver antenna 21R as illustrated in FIG. 7. In this modification example, the transmitter antennas 21T and 22T transmit electric waves such that a constructive interference occurs near the measurement part A, and the receiver antenna 21R receives an electric wave reflected by the measurement part A. Such a modification example also achieves effects similar to those of the above-described exemplary embodiment.

In addition, in the modification example illustrated in FIG. 7, the angles θ1 and θ2 of the transmitter antennas 21T and 22TT and 22T may each be changed in adjusting the distances L1 and L2 from the transmitter antennas 21T and 22T to the measurement part A.

In the above exemplary embodiment, the first antenna unit 21 and the second antenna unit 22 are connected to the single radar 23; however, the invention is not limited thereto. For instance, the radar apparatus 1 may include the radar 23 connected to the first antenna unit 21 and another radar 23 connected to the second antenna unit 22. In such a modification example, since respective Doppler signals (the I signal and the Q signal) are outputted from the two radars 23, it is favorable that the signal processor 31 be configured to be able to process each of four signals in total. In addition, the Doppler signals outputted from the two radars 23 may be subjected to a superimposition process or selectively used.

In the above exemplary embodiment, electric waves having the same phase are outputted from the two transmitter antennas 21T and 22T; however, the invention is not limited thereto. For instance, electric waves having opposite phases may be outputted from the two transmitter antennas 21T and 22T. In such a modification example, as the conditions for causing occurrence of a constructive interference between the electric waves, a difference between the distance L1 and the distance L2 may be adjusted to be an integral multiple of an odd multiple of one half of the wavelength λ of the electric wave.

In the above exemplary embodiment, description is made on the case where the measurement target for the radar apparatus 1 is a living body such as a human being or an animal and a fine motion (a change) of a skin surface of a breast accompanying respiration of the living body is to be detected; however, the invention is not limited thereto. For instance, in the above exemplary embodiment, the signal processor 31 may not only extract a frequency component corresponding to respiration from a Doppler signal obtained from the radar 23 but also extract a frequency component corresponding to a heartbeat.

In addition, the invention is not limited by the measurement target being a living body and is applicable to radar apparatuses that detect changes (for instance, a state of vibration and a displacement) of various measurement targets.

What is claimed is:

1. A radar apparatus comprising:
a first transmitter antenna configured to transmit a first electric wave having a first frequency to a measurement part of an object in a first transmission direction from a first position;
a second transmitter antenna configured to transmit a second electric wave having the first frequency to the measurement part in a second transmission direction from a second position different from the first position of the first transmitter antenna;
a receiver antenna configured to receive the first electric wave and the second electric wave, between which a constructive interference occurs and which are obtained by reflecting at the measurement part, and output a reception signal;
a radar configured to output a Doppler signal on a basis of the reception signal; and
a detector configured to detect a change in the measurement part on a basis of the Doppler signal, wherein
the first transmission direction and the second transmission direction intersect with each other, and the first and second transmission directions are adjusted to cause the constructive interference to occur between the first electric wave and the second electric wave at a location adjacent to the measurement part,
a first angle between the first transmission direction and a reference line is denoted by θ1, a second angle between the second transmission direction and the reference line is denoted by θ2, and the first and second angles satisfy 0°<θ1<90° and 0°<θ2<90°, where the reference line is perpendicular to a surface of the measurement part,
in a case in which the first and second electric waves have the same phase:
a first distance between the first position and the measurement part is equal to a second distance between the second position and the measurement part; or
a first difference between the first and second distances is equal to an integral multiple of a wavelength of the first frequency, and
in a case in which the first and second electric waves have opposite phases, a second difference between the first and second distances is equal to an integral multiple of an odd multiple of one half of the wavelength of the first frequency.

2. The radar apparatus according to claim 1, further comprising:
a first antenna unit including the first transmitter antenna; and
a second antenna unit including the second transmitter antenna, the first antenna unit and the second antenna unit each including the receiver antenna.

3. The radar apparatus according to claim 2, wherein
the measurement part of the object is a chest of a living body, and
the detector is configured to detect minute movements or fluctuations as the change of an outer surface of the chest caused by respiration of the living body.

4. The radar apparatus according to claim 3, wherein
the first frequency is 24 GHZ,
the detector is configured to extract a frequency component corresponding to the respiration of the living body from the Doppler signal to detect the minute movements or the fluctuations as the change, and
the frequency component corresponds to a range of 0.1 Hz to 0.5 Hz.

5. The radar apparatus according to claim 1, wherein
the measurement part of the object is a chest of a living body, and
the detector is configured to detect minute movements or fluctuations as the change of an outer surface of the chest caused by respiration of the living body.

6. The radar apparatus according to claim 5, wherein
the first frequency is 24 GHZ,
the detector is configured to extract a frequency component corresponding to the respiration of the living body from the Doppler signal to detect the minute movements or the fluctuations as the change, and
the frequency component corresponds to a range of 0.1 Hz to 0.5 Hz.

\* \* \* \* \*